US006007769A

United States Patent [19]

Lance-Gómez et al.

[11] Patent Number: 6,007,769

[45] Date of Patent: *Dec. 28, 1999

[54] SINGLE-PHASE SOAP COMPOSITIONS

[75] Inventors: E. Theodore Lance-Gómez; Mark M. Gipp, both of Racine, Wis.; Robert Y. Lochhead, Lamar, Miss.; Charles E. Seaman, Jr., Kenosha, Wis.

[73] Assignee: S. C. Johnson & Son, Inc., Racine, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/855,087

[22] Filed: May 13, 1997

Related U.S. Application Data

[60] Continuation of application No. 08/463,421, Jun. 5, 1995, abandoned, which is a division of application No. 08/301,213, Sep. 6, 1994, abandoned.

[51] Int. Cl.[6] .................................................. A61L 9/00

[52] U.S. Cl. ................................ 422/4; 422/5; 424/76.3; 424/76.4

[58] Field of Search ...................... 422/1, 4, 5; 424/76.1, 424/76.3, 76.4; 512/1, 2, 4

[56] References Cited

U.S. PATENT DOCUMENTS

| | | | |
|---|---|---|---|
| 4,178,264 | 12/1979 | Streit et al. | 252/316 |
| 4,666,671 | 5/1987 | Purzycki et al. | 422/5 |
| 4,732,693 | 3/1988 | Hight | 252/132 |
| 4,975,218 | 12/1990 | Rosser | 252/117 |
| 5,034,222 | 7/1991 | Kellett et al. | 424/76.4 |
| 5,324,490 | 6/1994 | Van Vlahakis et al. | 422/5 X |
| 5,419,879 | 5/1995 | Vlahakis et al. | 422/5 X |

*Primary Examiner*—Krisanne Thornton

[57] ABSTRACT

The present invention relates to single-phase soap gels and viscous soap compositions which are produced by alkanolamine neutralization of a fatty acid above the Krafft point. These compositions are robust, biodegradable, and are insensitive to temperature changes. The compositions also exhibit excellent cleaning properties and may be used as laundry cleaning agents, oven cleaners, hard surface cleaners, and disinfectants and air fragrancing compositions.

17 Claims, 11 Drawing Sheets

SINGLE-PHASE SOAP COMPOSITIONS

CROSS-REFERENCE TO RELATED APPLICATIONS

This is a continuation of Ser. No. 08/463,421 filed Jun. 5, 1995, now abandoned, which in turn is a division of Ser. No. 08/301,213 filed Sep. 6, 1994 now abandoned.

FIELD OF THE INVENTION

This invention relates to single-phase soap-based compositions for use in cleaning and air fragrancing products.

BACKGROUND ART

Soap-based cleaning compositions traditionally rely on neutralization of a fatty acid with an alkali metal, alkaline earth metal, amine or alkanolamine, such as monoethanolamine ("MEA") or triethanolamine ("TEA"). These compositions provide non-gelled dispersions of the soap in the remaining matrix, usually because the soap is below its Krafft point at ambient conditions. The Kraffi point is the temperature above which the solubility of a surfactant increases sharply (i.e., micelles begin to be formed). Unfortunately, these traditional soap dispersions are opaque and can be inhomogeneous. Alternatively, a hard soap cake or bar is formed. In either case, these soaps contain a majority of solidified components, with water being a lesser constituent at approximately from 15–40% by weight. The soap may itself be a smaller fraction of about 25–50% by weight. For a liquid soap, the same behavior typically occurs with a soap concentration of about 15% by weight. Accordingly, it has been difficult for the industry to economically produce soap-based compositions which can readily assimilate a wide variety of compounds while maintaining homogeneity.

Accordingly, it is an object of the present invention to provide homogeneous soap-based compositions at a broad range of soap concentrations.

It is an additional object of the present invention to provide soap-based compositions that can be optically transparent.

It is a further object of the present invention to provide soap-based compositions that can readily incorporate anionic and nonionic surfactants, solvents, and ionic salts.

It is also an object of the present invention to provide soap-based compositions that are insensitive to wide temperature changes.

It is a further object of the present invention to provide soap-based compositions which are biodegradable.

SUMMARY DISCLOSURE OF THE INVENTION

The present invention meets these objectives and others by providing liquid single-phase soap gels and viscous soap compositions by alkanolamine neutralization of a fatty acid resulting in a soap solution above the Krafft temperature. Surprisingly, a rubbery gel is formed with the alkanolamine at from about 2.0% to about 8.0% by weight concentration of fatty acid. Higher or lower concentrations of fatty acid result in the formation of viscous liquids. Unexpectedly, the addition of certain solvents and/or surfactants also results in the formation of a gelled soap phase.

These soap systems of the present invention are thermally stable to about 80° C. These biodegradable soap compositions also exhibit excellent cleaning properties in laundry cleaning agent compositions, grease and oil removal, glass/hard surface cleaning and oven cleaning. In addition, the soap-based compositions of the present invention may be utilized as air fragrancing gels and disinfectant compositions.

BRIEF DESCRIPTION OF THE DRAWINGS

Where full identification of the different liquid crystal characterizations on the following phase diagrams could not be provided, abbreviations were used.

Detailed Description of the Invention

The morphology of soap compositions can be described in terms of lamellar ("D"), reverse micellar ("RD"), hexagonal ("E"), reverse hexagonal ("RE"), cubic ("C") and isotropic phases ("I") and emulsions ("EM") which describe how the soap molecules structure themselves in solution.

Soaps are amphipathic molecules consisting of a hydrophilic head group and a hydrophobic tail group. When soaps are placed in water, the hydrophobic tail group preferentially adsorb at the air-water interface by hydrophobic interaction. This adsorbed hydrophobic portion of the soap lowers the surface tension. As soap concentration increases, the surface tension continues to decrease. At a critical concentration, the hydrophobic tail groups aggregate together and micelles form. This concentration is called the critical micelle concentration (CMC).

Micelles have a structure in which the hydrophobic groups are located in the center of the aggregates and the hydrophilic groups at the surface of the aggregates where they can interact with water in the bulk phase. The shape of micelles is controlled by the principle of opposing forces. These opposing forces are the interaction of the hydrophobes that causes micellar aggregation and the repulsion of the head groups.

Repulsion between the head groups is diminished as the soap concentration increases, as salt is added to aqueous solutions of ionic surfactants, by the addition of amphipathic molecules with small head groups, or by an increase in temperature for certain soaps. As repulsion between the head groups decreases, the curvature at the micelle surface is lowered and the micelles, perforce, change shape. As repulsion between the head groups decreases, the micelles are not constrained in spherical geometry, thus, may adopt ellipsoidal and eventually cylindrical structures. These cylinders can become infinitely long on a molecular scale and, if present in sufficient concentrations can pack into a hexagonal array to form hexagonal liquid crystal striations.

Figure 11A:
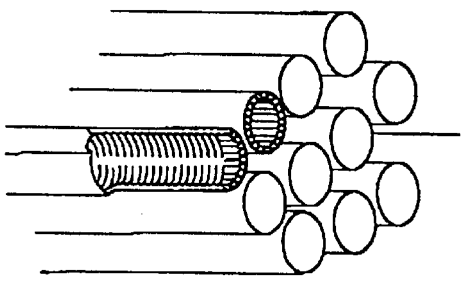
FIG. 11A illustrates the hexagonal liquid crystal phase.
Figure 11B:
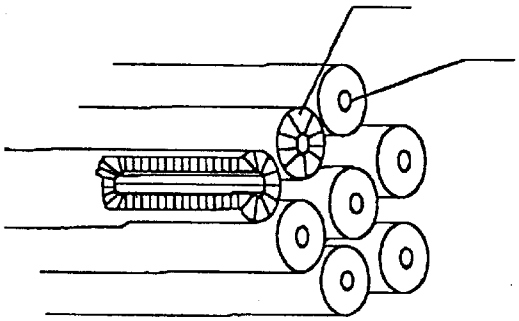
FIG. 11B illustrates the reverse (or inverse) hexagonal liquid crystal phase.

Hexagonal phase liquid crystals (FIG. 11A) are rod-shaped micelles that are packed in a hexagonal array and separated by a continuous water region. Hexagonal liquid crystals are indefinite in length and flow uniaxially. Reverse (or inverse) hexagonal phase liquid crystals (FIG. 11B) are similar to the hexagonal except the hydrophobic tail groups are in the continuous phase.

Figure 11C:
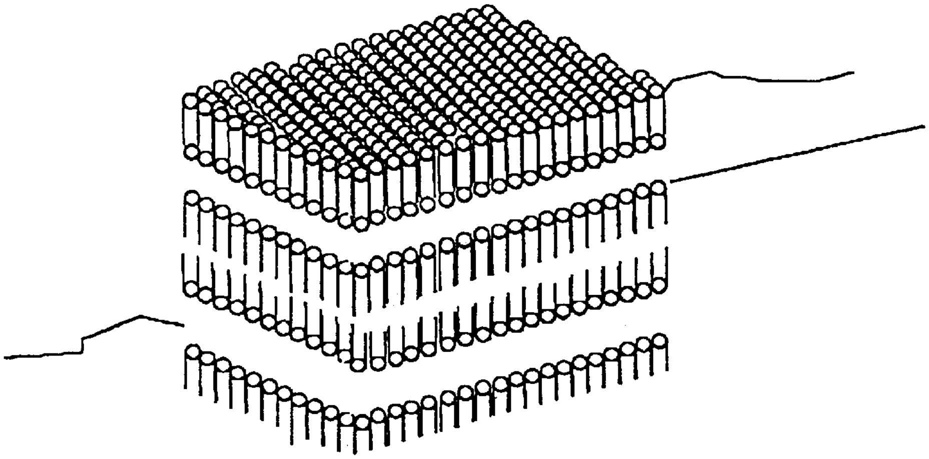
FIG. 11C illustrates the lamellar liquid crystal phase.

Further decrease in the repulsion between the head groups eventually causes the surfactant to be arranged in infinite bilayers called the lamellar liquid crystal phase (FIG. 11C). Lamellar phase liquid crystals have lipid layers that move over each other easily to give a lubricant rheology.

Cubic phase liquid crystals are also known as viscous isotropic. Since this phase is isotropic, cubic phases are not birefringent. There are two types of cubic phase liquid crystal: normal or water continuous, and reversed or alkyl chain continuous. Cubic phase liquid crystals have a rigid gel rheology because there is no easy flow in any direction. Liquid crystals can be characterized by polarized light microscopy as each has a distinct pattern under the polarized light microscope.

The liquid crystal characterization of the compositions of the present invention (FIGS. 1, 3–4 and 7–10) and prior art (FIGS. 2 and 5) are illustrated by ternary phase diagrams. See FIGS. 1–10. Ternary phase diagrams for FIGS. 1–4 are read as each apex is 100% by weight and the baseline opposite each of the apex is 0% by weight of that component. Ternary phase diagrams for FIGS. 5–10 are read as the concentration range for oleic acid and AMP is 0% to 30%; the concentration range for water is 70% to 100%. The apex containing each ingredient label represents the point of highest concentration for that component. The concentration for oleic acid and AMP diminishes to 0% proceeding to the apex containing the label for water.

The present invention relates to the formation of temperature stable liquid crystals or micellar compositions by combining a fatty acid neutralized with a select alkanolamine, an effective amount of water to achieve a hydrophobic-hydrophilic balance necessary for liquid crystal formation, and from about 0.5% to about 15.0% by weight of at least one nonionic surfactant or from about 1.0% to about 35% by weight of a compound selected from the group consisting of water-soluble solvents, oil-soluble solvents and mixtures thereof The soap-based compositions of the present invention can readily incorporate a compound selected from the group consisting of anionic surfactants, ionic salts and mixtures thereof, while maintaining homogeneity.

A first step in producing the single-phase soap gels and viscous soap compositions of the present invention is the alkanolamine neutralization of a fatty acid to yield a composition above the Krafft point of the soap. Other ingredients are then added to form the compositions of the present invention.

Generally any fatty acid may be used in the soap compositions of the present invention. Suitable fatty acids include saturated or unsaturated fatty acids having a carbon chain length of $C_8$–$C_{30}$, preferably $C_{10}$–$C_{20}$, and most preferably $C_{12}$–$C_{16}$. These fatty acids include lauric acid, stearic acid, oleic acid, palmitic acid, coconut oil, tallow oil, myristic acid and mixtures thereof. The fatty acid chosen typically depends upon the use of the soap composition. For example, for a laundry cleaning agent, typically oleic acid.

Generally, any amount of fatty acid may be used to produce the soap-based compositions of the present invention. Preferably, from about 0.1% to about 90% more preferably from about 3.0% to about 18% by weight of fatty acid may be used. Most preferably, from about 2 to about 8% of fatty acid is used to produce soap gels having a rubber-like rheology.

The alkanolamine used for the neutralization of the fatty acid is a critical element of the present invention. Suitable alkanolamines include triethanolamine ("TEA") and monoethanolamine ("MEA") available from Dow Chemical Co. as well as diisopropanolamine and diethanolamine. More preferably, the alkanolanine is selected from the group consisting of 1-amino-2-methyl-1-propanol ("AMP") and 2-amino-1-butanol ("AB") both available from Angus Chemical; tetrahydroxypropylethylenediamine ("TE") available under the trade name Neutrol TE from BASF Co.; triisopropanolamine ("TIPA") available from Dow Chemical Co. More preferably the alkanolamine is selected from the group consisting of AMP; AB; Neutrol TE and TIPA. 2-amino-2-methyl-1,3-propanediols are not useful in the present invention, as they do not produce a soap composition having the desired rheological or other physical characteristics of the present invention.

Producing soap from alkanolamine neutralization of fatty acid is well known in the art. U.S. Pat. No. 4,975,218 to Rosser discloses an aqueous single liquid phase detergent which contains from 10 to 50% by weight of at least one $C_{12}$–$C_{18}$ fatty acid soap which may be formed from the addition of an alkanolamine such as triethanolamine. However, the '218 patent does not teach or suggest robust soap compositions, which are also stable to high temperatures, or that the desired rheological and/or visual properties may be achieved by a low concentration of an alkanolamine in the neutralization process.

Another example of soap gel produced by alkanolamine neutralization of a fatty acid is described in U.S. Pat. No. 3,541,581 to Monson, which contains essentially 40% to about 90% by weight of water and about 4.0% to about 25% by weight of water-soluble soap. The Monson patent does not teach or suggest soap compositions possessing the thermal stability or robust nature of the present invention.

Surprisingly, the addition of nonionic surfactants, oil-soluble solvents or water-soluble solvents enhance a liquid crystal, or ordered structure and thermal characteristics of soap based compositions. This allows the robust compositions of the present invention to be used in a wide variety of applications such as laundry cleaning agents, air freshener gels, oven cleaners and the like.

For example, nonionic surfactants have a positive effect on the liquid crystal characteristics of the soap-based compositions of the present invention. Suitable nonionic and anionic surfactants for use in the present invention are typically chosen according to the particular use of a product. For example, suitable nonionic surfactants in laundry cleaning agents using the single-phase soap composition of the present invention include long chain alcohols, such as linear ethoxylated and linear propoxylated alcohols; sorbitan surfactants, such as sorbitan monooleate, sorbitan monolaurate, sorbitan trioleate, such as the Tweens from ICI America and the sorbitan fatty acid esters, such as the Spans from ICI America; ethoxylated nonylphenols, such as the Surfonic N series available from Texaco; the ethoxylated octylphenols, including the Triton X Series available from Rohm & Haas; the ethoxylated secondary alcohols, such as the Tergitol Series available from Union Carbide; the ethoxylated primary alcohols series, such as the Neodols available from Shell Chemical; the polymeric ethylene oxides, such as the Pluronics available from B.A.S.F. Wyandotte.

Unexpectedly, the preferred nonionic surfactant for use in the present invention is ethoxylated $C_{12}$–$C_{14}$ linear alcohol having 4 moles ethylene oxide ("EO") available under the trade name Surfonic L24-4 or ethoxylated $C_{12}$–$C_{14}$ linear alcohol having 9 moles EO available under the trade name Surfonic L24-9. Both nonionics are available from Texaco. One of ordinary skill would expect that a nonionic surfactant having a hydrophilic substituent, i.e., long chain EO, such as Surfonic L24-9, would tend to associate with the water in the formulations, causing a phase separation of the gel, or at least undesirably reducing the viscosity of the final solution. Similarly, nonionic surfactants having short chain EO, such as Surfonic L24-4, one of ordinary skill would expect the surfactant to act as a solvent, also resulting in phase separation of the gel. Therefore, it is surprising that the addition of these nonionic surfactants produces viscous single-phase liquids and particularly that Surfonic L24-9 provides gelled soap-based compositions.

Typically, the nonionic surfactant is present in an amount from about 0.5% to about 20%, preferably, from about 2.0% to about 10%, and most preferably, from about 3.0% to about 5.0% by weight of the composition.

Figure 1:
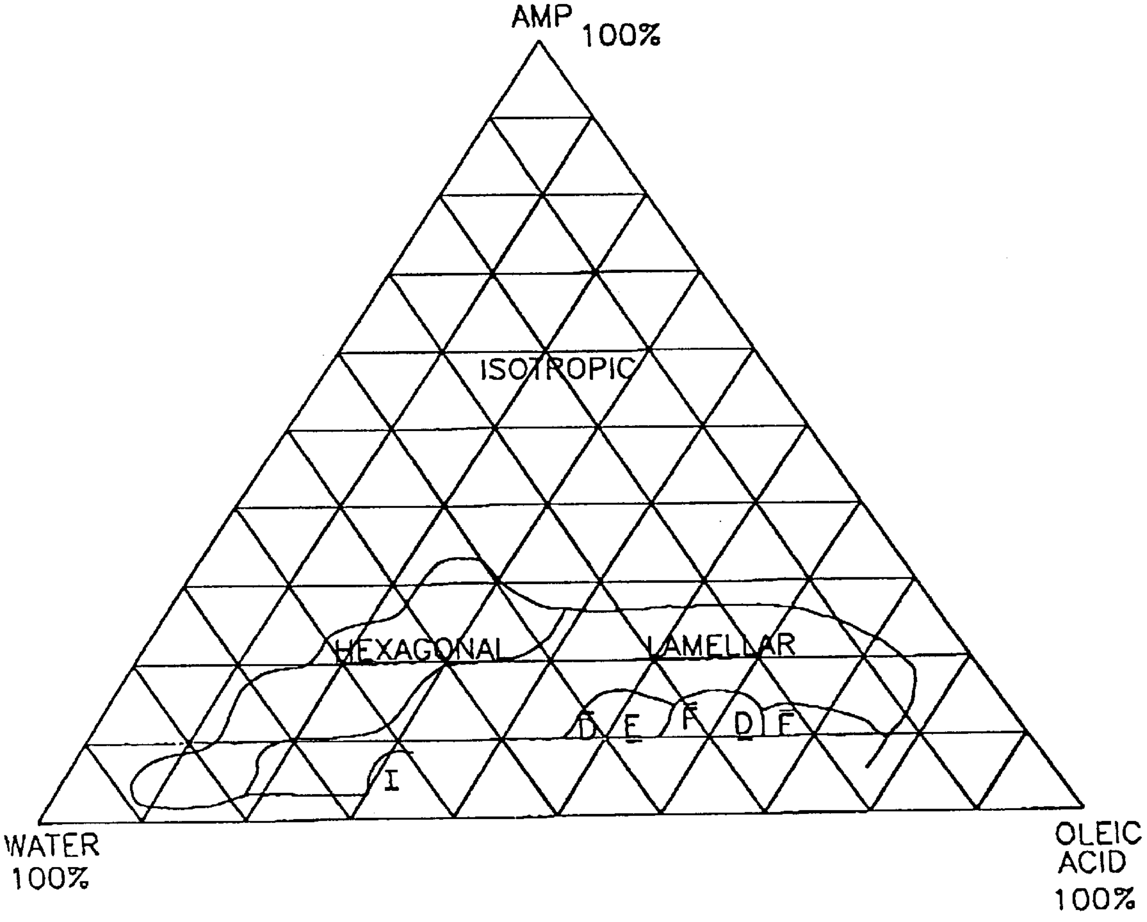
FIG. 1 is a phase diagram showing the liquid crystal characterization of the oleic acid soap compositions of the present invention having 5.0% by weight of $C_{12}$–$C_{14}$ linear alcohol ethoxylate, having 9 moles EO.
Figure 2:
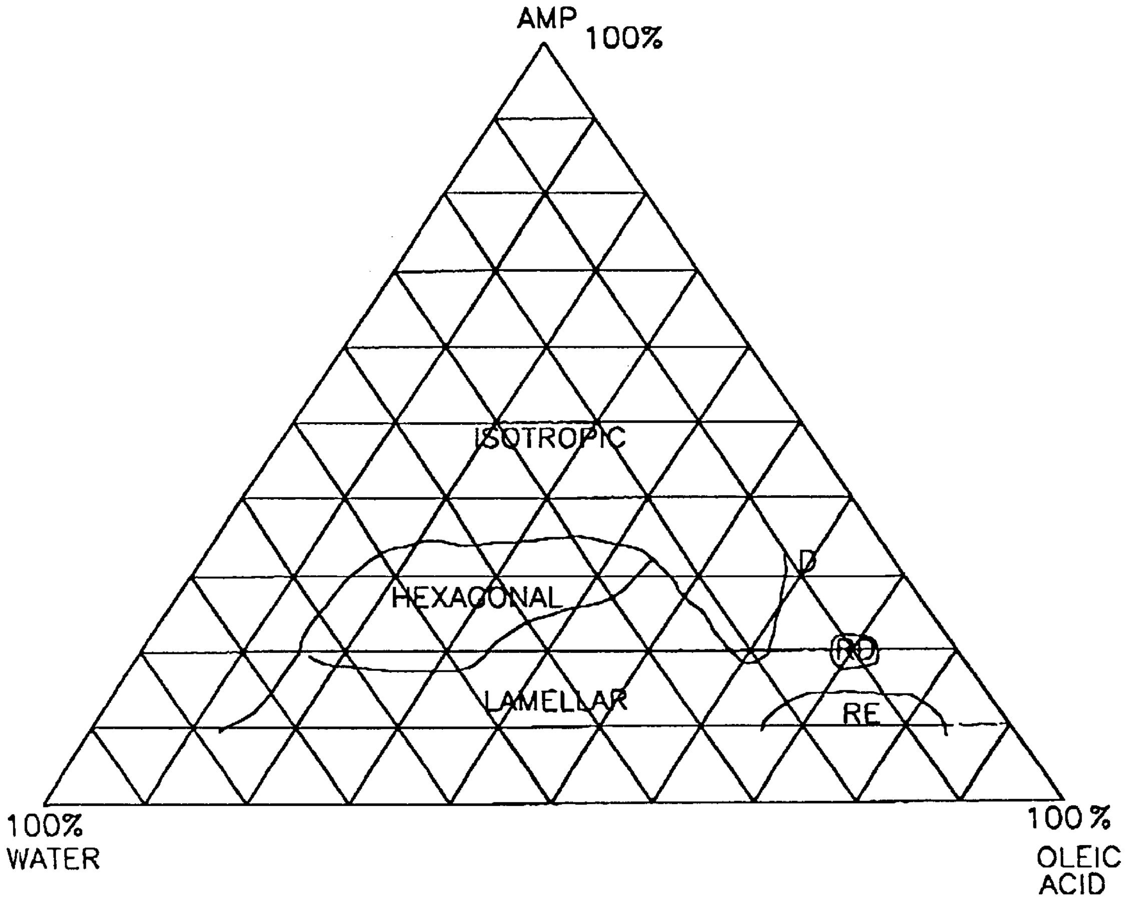
FIG. 2 PRIOR ART
FIG. 2 is a ternary phase diagram of the liquid crystal characterization of prior art oleic acid soap compositions.
Figure 3:
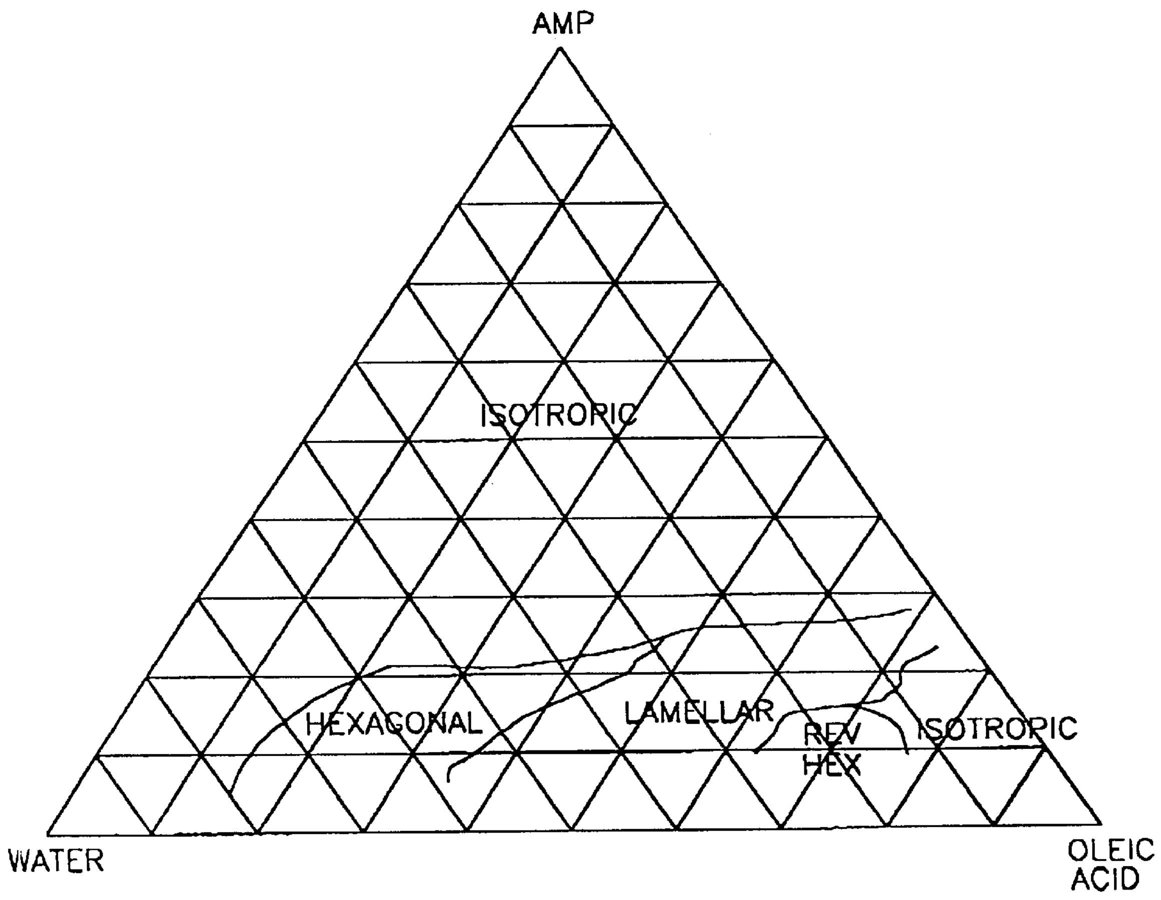
FIG. 3 is a quaternary phase diagram of the liquid crystal characterization of oleic acid soap compositions of the present invention having 5.0% by weight of butyl carbitol at 25° C.

To illustrate the enhancement of the liquid crystal structures of the soap compositions of the present invention by the addition of nonionic surfactants, FIG. 1 is a phase diagram showing the liquid crystal characterization of an oleic acid/AMP soap compositions to which 5.0% by weight of Surfonic L24-9 has been added. Upon comparing these results with those soap samples without Surfonic L24-9 as shown in FIG. 2, it is clear that soap gel formation is achieved at lower concentrations of both AMP and oleic acid with the addition of a nonionic surfactant to the compositions.

Surprisingly, the addition of water-soluble or oil-soluble solvents to the soap-based compositions of the present invention unexpectedly enhances structure, and particularly in some systems the liquid crystal characteristics of the compositions and does not destroy the systems. Suitable water-soluble solvents include alkylene glycol ethers such as ethylene glycol monobutyl ether ("butyl Cellosolve"), ethylene glycol monohexyl ether ("hexyl Cellosolve"), diethylene glycol monobutyl ether available under the name "butyl carbitol"available from Texaco, and alcohols such as isopropanol. Preferably, the water-soluble solvent is a glycol ether.

Suitable oil-soluble solvents for use in the present invention include d-limonene and terpene-based solvents such as the low flash point terpene-based solvent available under the tradename Glidsol 90 from GlidCo; cyclohexane available from Fisher Chemical and unsaturated/saturated $C_4$–$C_{30}$ hydrocarbons such as the alpha-olefin, tetradecene, available under the trade name Neodene 14 from Shell or Gulftene 14 from Chevron. Solvents containing volatile organic compounds ("VOCs"), such as cyclohexane, are not generally not preferred in view of environmental constraints.

Due to the robust nature of the present invention, oil-soluble fragrance oils are also compatible with the present soap-based systems and, may also act as solvents in the soap-based compositions. Thus, when preparing air fragrancing systems using the present invention, no other solvents are needed.

Solvent is typically present in an amount from about 0% to about 60%, preferably from about 1.0% to about 35%, and most preferably, from about 5.0% to about 25% by weight of the composition.

Figure 4:
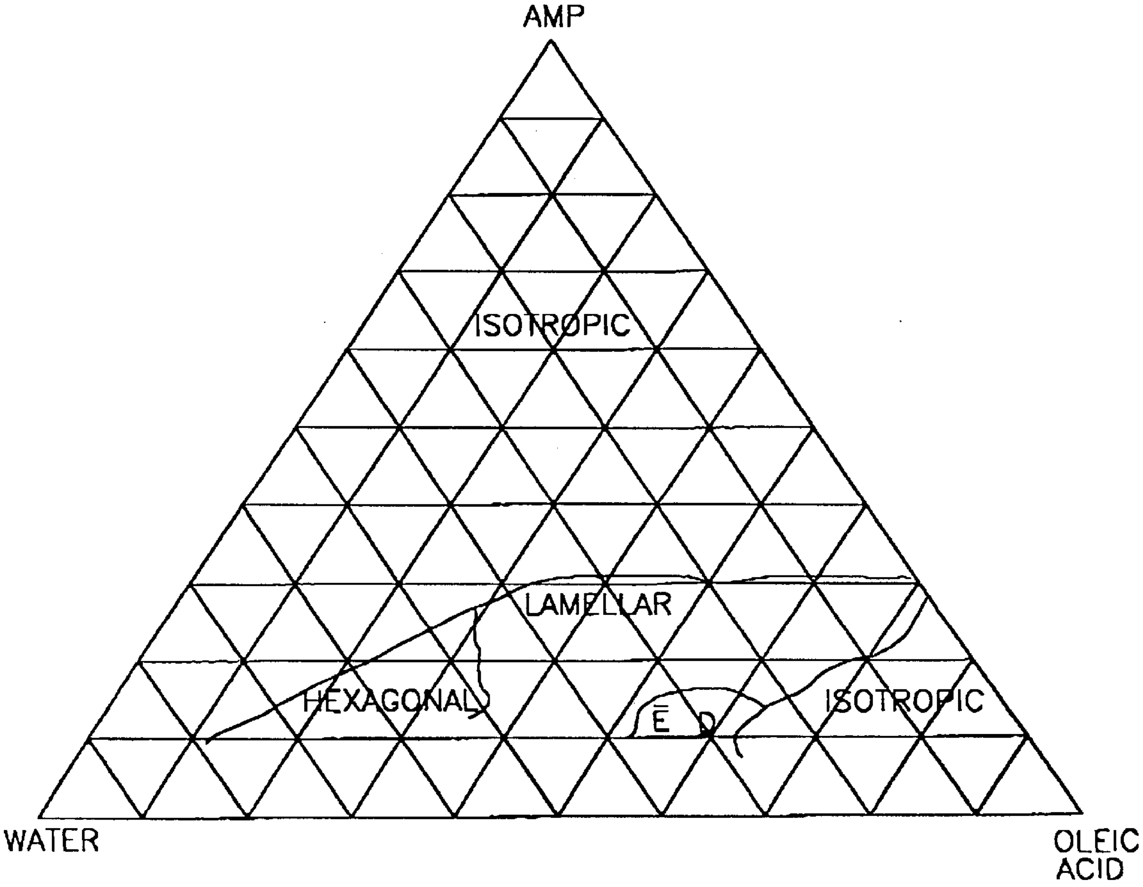
FIG. 4 is a phase diagram illustrating the liquid crystal characterization of oleic acid soap compositions of the present invention at 25° C. having 5.0% by weight butyl carbitol and 5.0% by weight of ethoxylated $C_{12}$–$C_{14}$ linear alcohol having 9 moles EO.

As shown in FIG. 4, the addition of 5.0% by weight of butyl carbitol to the oleic acid/AMP soap compositions of the present invention allows the formation of a soap gel at lower concentrations of AMP and oleic acid than the prior art compositions without butyl carbitol as illustrated in FIG. 2.

FIG. 4 illustrates the changes in the liquid crystal character of adding both nonionic surfactant such as Surfonic L24-9 and a water-based solvent such as butyl carbitol to the soap-based compositions of the present invention.

An effective amount of water is necessary to achieve the hydrophobic-hydrophilic balance necessary for liquid crystal formation. Water is present in a wide range of amounts depending on the type of application for the soap composition of the present invention. For example, in an oven cleaning composition, water is typically present in an amount from about 5% to about 94%, preferably from about 5% to about 85% and most preferably from about 20% to about 60% by weight of the composition.

Anionic surfactants and salts that ionize in water ("ionic salts") may also be added without negatively affecting the rheological characteristics of the present compositions.

One of ordinary skill would expect the formation of solid particles in the compositions by the addition of anionic surfactants to the soap compositions of the present invention. This formation of solid particles would lead to the phase separation and the ultimate destruction of the system. Thus, it is surprising that the addition of anionic surfactants to the soap-based compositions of the present invention does not result in destruction or phase separation of the gelled structure.

Typical ionic salts which can be used in the present invention include salts of chlorides, silicates, citrates, phosphates, borates, zeolites, nitrilotriacetic acid ("NTA"), ethylenediaminetetracetic acid ("EDTA") and mixtures thereof. Examples of these ionic salts include sodium chloride, sodium citrate and sodium silicate. Ionic salts are typically present in an amount from about 0% to about 25%, preferably from about 0.2% to about 20%, and most preferably from about 1.0% to about 15% by weight of the composition.

Suitable anionic surfactants for use in, for example, a glass cleaning composition, include sulfonates such as alkylbenzene sulfonate, and sulfates such as lauryl sulfate and lauryl ether sulfate. Additional anionic surfactants include alcohol carboxylates such as trideceth-7 carboxylic acid available under the trade name Sandopan DTC Linear P from Sandoz. Typically, the anionic surfactant is present in an amount from about 0% to about 15%, preferably, from about 2.0% to about 5.0%, most preferably, about 5.0% by weight of the composition.

Additional optimal components include solid particles which may be suspended in the soap-based compositions to create abrasive cleaning compositions. Typical abrasive materials which may be added to the compositions of the present invention include calcium silicate, insoluble silicate and calcium carbonate.

Further optional ingredients may be added which are conventionally employed such as antibacterial agents and preservatives, fragrances and colorants. As the soap-based compositions of the present inventions are biodegradable, non-biodegradable optional components are not preferred.

The soap-based compositions of the present invention can be prepared by any conventional means. However, when optical testing is desired, the following annealing procedure is recommended to assure that an equilibrium has been achieved in the system. First, prepare the compositions at room temperature of about 20° C., then store the compositions for 24 hours in a 60° C. water bath. Next, agitate the composition by shaking in a styrofoam insulated container, then take to a temperature of observation and immediately examine by polarizing microscopy. The samples may be examined one month after preparation to verify that the structure reported is indeed the equilibrium structure.

The compositions of the present invention will now be illustrated by the following examples, wherein all parts and percentages are by weight and all temperatures in degree Celsius, unless otherwise indicated:

EXAMPLES 1–6

Laundry Cleaning Agents

Laundry cleaning agents having the following compositions were prepared by cold blending the ingredients:

For compositions containing coconut fatty acid, the fatty acid was melted before neutralization with AMP.

| Ingredients | Ex. 1 % | Ex. 2 % | Ex. 3 % | Ex. 4 % | Ex. 5 % | Ex. 6 % |
|---|---|---|---|---|---|---|
| Coconut Fatty Acid | 15.0 | 15.0 | — | — | — | — |
| Oleic Fatty Acid | — | — | 15.0 | 5.0 | 15.0 | 15.0 |
| Ethoxylated Linear $C_{12}$–$C_{14}$ Alcohol, 4 Moles EO (Surfonic L24-4) | 5.0 | — | 5.0 | 5.0 | — | — |
| Sodium Citrate | — | 1.0 | — | — | — | — |
| AMP | 5.57 | 5.57 | 5.03 | 1.26 | 5.42 | 5.42 |
| Tetradecene (Neodene 14) | — | — | — | — | 5.0 | — |
| Diethylene Glycol Monobutyl Ether (Butyl Carbitol) | — | — | — | — | — | 5.0 |
| Water | qs | qs | qs | qs | qs | qs |

EXAMPLE 7

Oven Cleaning Composition

This example illustrates a viscous gel intended for application from a trigger spray dispenser for use in oven cleaning. The composition contained the following ingredients:

| Ingredient | % |
|---|---|
| Oleic Fatty Acid | 9.0 |
| AMP | 3.0 |
| Ethoxylated $C_6$–$C_{10}$ linear alcohol (50% EO) (Alfonic 610-3.5) | 6.0 |
| Metasilicate | 6.0 |
| Hexyl Cellosolve | 2.5 |
| Water | qs |

The oven cleaning composition was prepared by first neutralizing the oleic acid with AMP. Next, the ethoxylated $C_6$–$C_{10}$ linear alcohol and hexyl Cellosolve, then water, and finally metasilicate were added to the soap.

Comparative Example

The following 1.0.g amount of soil composition was spread evenly across an 8"x14"carbon steel surface and baked in an oven for 25 minutes at 230–245° C:

| Ingredient | Parts |
|---|---|
| Beef tallow | 4 |
| Lard | 4 |
| Sugar | 2 |
| Powdered Whole Egg | 1 |

The Beef tallow consisted of the melted portion of beef fat from butcher trimmings. The powdered whole egg was Primex 10 available from Primegg, Ltd. The sugar consisted of refined cane sugar and the lard is available from Oscar Mayer. The plate was then allowed to cool to room temperature before each cleaning composition was applied.

The comparative study was performed between the oven composition of the present invention and a commercially available non-caustic formula, Easy-Off® Non-Caustic Formula (Fume-Free). The directions on the back of the Easy-Off® bottle were followed:

First, the Easy Off® bottle was well shaken and the Easy-Off® formula was evenly applied to over one-half of the soiled carbon-steel plate. The other half of the soiled plate was coated with Example 7 of the oven cleaning formulation of the present invention.

The plate was then placed into a preheated oven and baked for about 30 minutes at 240° C. (475° F.). The plate was then removed from the oven and rinsed thoroughly under a faucet with warm water. The plate was then dried in a 120° C. oven for 2 minutes to inhibit rust formation.

It was observed that the side treated with Easy-Off® was about 92% clean. The plate was discolored and possibly etched. The side treated with the oven cleaning composition of the present invention was 98% clean with no discoloration or apparent damage to the plate.

In a separate test, 1g of the oven cleaning composition of the Example 7 formulation was placed on a soiled test panel at room temperature and left at room temperature for approximately 10 hours. The panel was rinsed thoroughly with warm water and allowed to air dry. The panel showed a high level of soil removal (approximately 97%) with no discoloration or etching of the plate.

Usually, due to the caustic nature of most current commercial oven cleaning products, the user must wait until the oven cools down before applying the cleaning product. If the user applies the caustic formulas to a hot oven, they will experience "flashback"of caustic vapors.

Advantageously, the oven cleaning compositions of the present invention are temperature stable to about 80° C. This allows the user to safely clean an oven without waiting for it to completely cool down. This is especially useful for restaurants and bakeries which rely on continuous use of their ovens.

EXAMPLE 8

Air Fragrancing Gel

This example illustrates an air fragrancing gel of the present invention.

| Ingredients | % |
|---|---|
| Oleic Fatty Acid | 15.0 |
| AMP | 5.52 |
| Lemon Fragrance Oil | 5.0 |
| Water | qs |

The air fragrancing gel was prepared by first neutralizing the oleic acid with AMP to provide the soap, then the fragrance was added to the soap and mixed well. Finally, the water was mixed into the composition.

EXAMPLES 9–12

Hard Surface Cleaning Composition

The following examples illustrate the hard surface cleaning compositions of the present invention.

| Ingredient | Ex. 9 | Ex. 10 | Ex. 11 | Ex. 12 |
|---|---|---|---|---|
| Oleic Fatty Acid | 0.5 | 0.5 | 0.5 | 0.5 |
| AMP | 0.185 | 0.185 | 0.185 | 0.185 |
| Hexyl Cellosolve | 0.5 | 0.5 | 0.5 | 0.5 |
| Butyl Cellosolve | 0.5 | 0.5 | 0.5 | 0.5 |
| Isopropanol | 2.0 | 4.0 | 2.0 | 4.0 |
| Sodium Dodecylbenzene Sulfonate | 0.2 | 0.2 | — | — |
| Aqueous Ammonia | 0.3 | 0.3 | 0.3 | 0.3 |
| Water | qs | qs | qs | qs |

The hard surface cleaning compositions were prepared by first neutralizing the fatty acid with the AMP. Next the remaining ingredients were mixed into the composition.

EXAMPLE 13

Disinfectant Composition

This example illustrates a disinfectant composition.

| Ingredients | % |
|---|---|
| Oleic Fatty Acid | 15.0 |
| AMP | 5.52 |
| Ethanol; 190 Proof | 77.78 |
| Water | qs |

The disinfectant composition was prepared by first neutralizing the fatty acid with AMP. Next the ethanol was added to the soap. Finally, the water was added and the composition mixed to provide an even distribution of the ingredients.

Temperature Studies

Liquid crystals are highly temperature dependent. Accordingly, liquid crystal phases associated with gels and viscous liquids such as hexagonal phases and lamellar phases have generally existed across a narrow temperature range. The soap compositions of the present invention have not only achieved these liquid phases at lower concentrations of alkanolamine neutralized fatty acid, they have maintained their structures across a broader temperature range than prior soap compositions.

To demonstrate this phenomenon, the physical and visual characteristics of the soap compositions of the present invention were determined by the following temperature studies with oleic acid:

The oleic acid samples were prepared at a temperature of about 20° C. The samples were prepared by adding the acid, water, solvents, and then the AMP. The samples were then stored for about 24 hours in a 25° C., 60° C., or 80° C. water bath. Next, each sample was agitated by shaking in an insulated styrofoam container. Then the samples were taken to a temperature of observation and immediately examined by polarizing microscopy. The samples were examined by polarizing microscopy after preparation to verify that the structure reported was the equilibrium structure. In addition, photomicrographs of the samples were taken.

Phase diagrams were prepared from the results of these temperature studies as shown in FIGS. 4–10.

Figure 5:
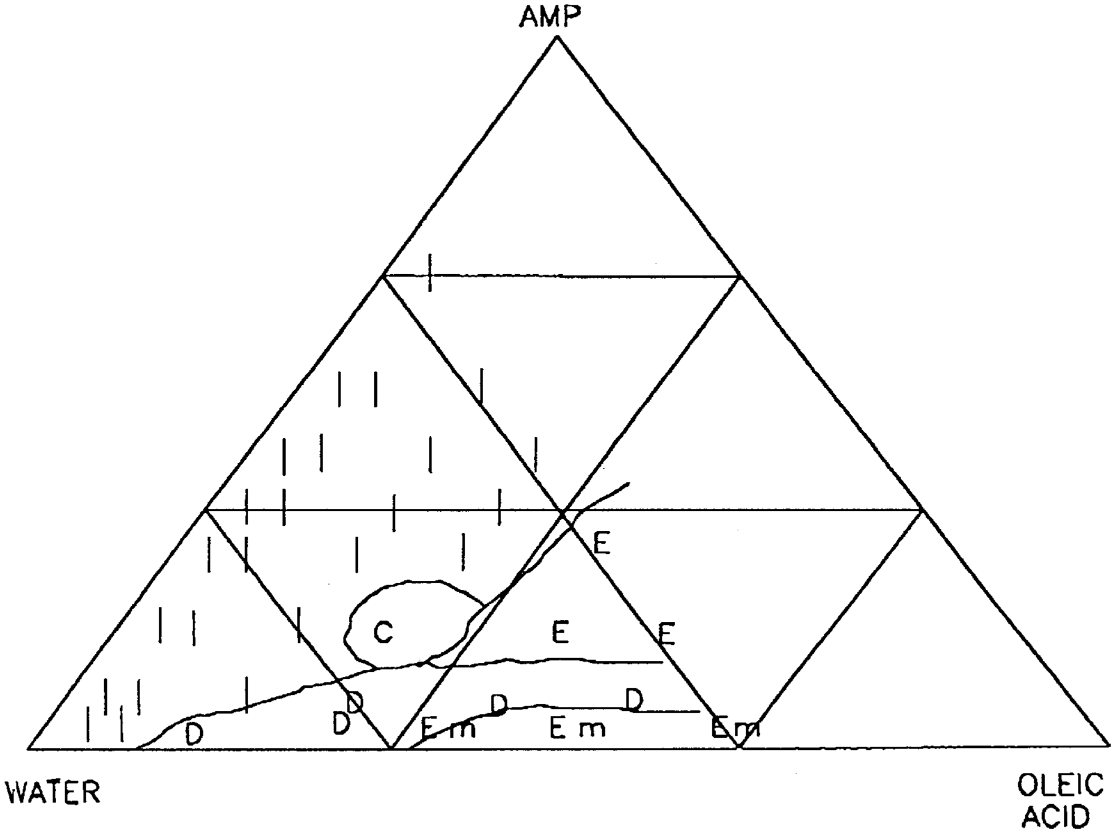
FIG. 5 PRIOR ART
FIG. 5 is a ternary phase diagram of the liquid crystal characterization of prior art oleic acid soap compositions.
Figure 6:
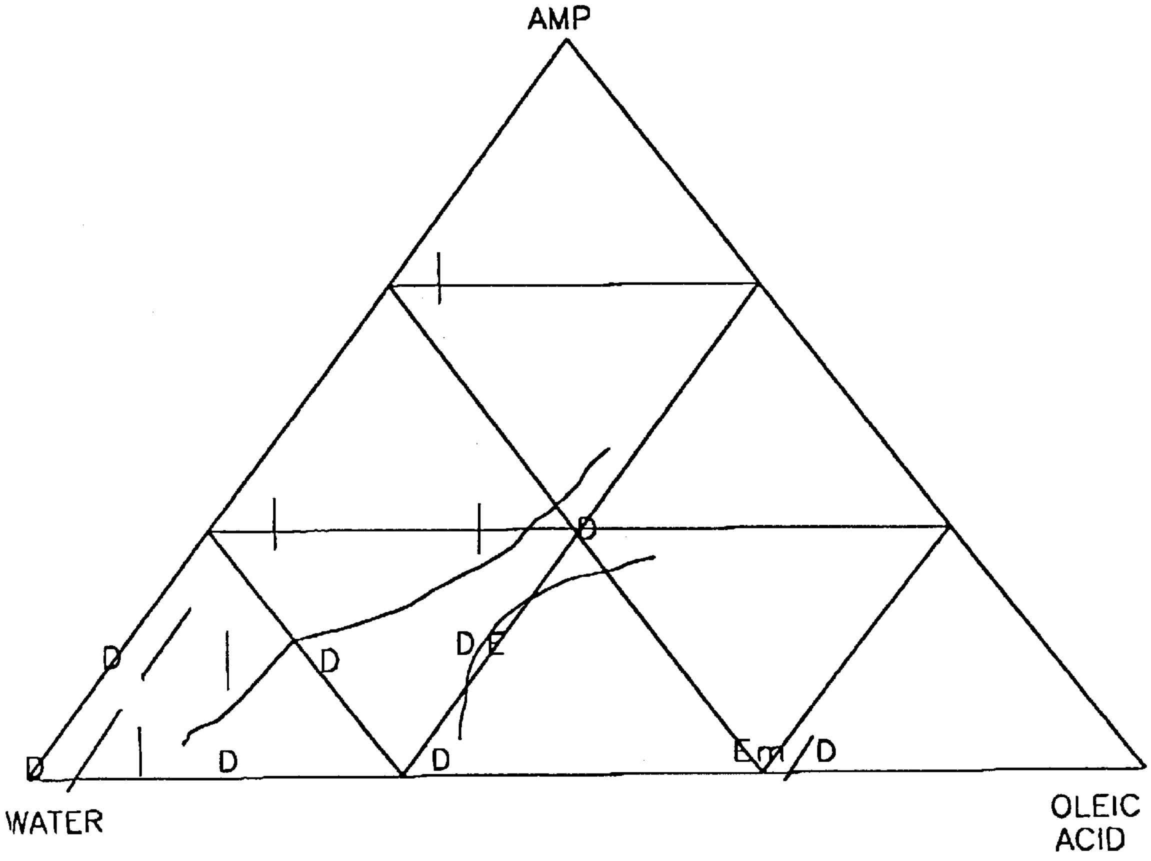
FIG. 6 is a phase diagram showing the liquid crystal characterization at 25° C. of the oleic acid soap compositions of the present invention having 5% by weight of $C_{12}$–$C_{14}$ linear alcohol ethoxylate having 4 moles EO.
Figure 7:
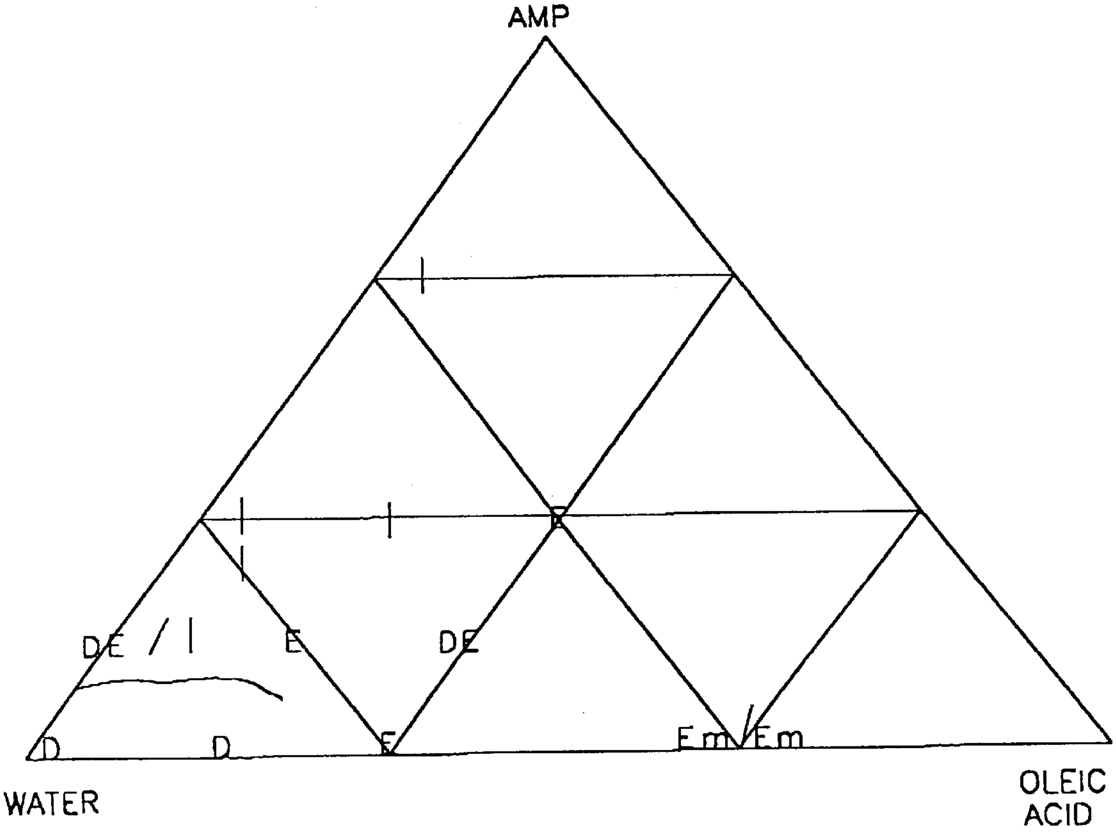
FIG. 7 is a phase diagram showing the liquid crystal characterization at 60° C. of the oleic acid soap compositions of the present invention having 5% by weight of $C_{12}$–$C_{14}$ linear alcohol ethoxylate having 4 moles EO.
Figure 8:
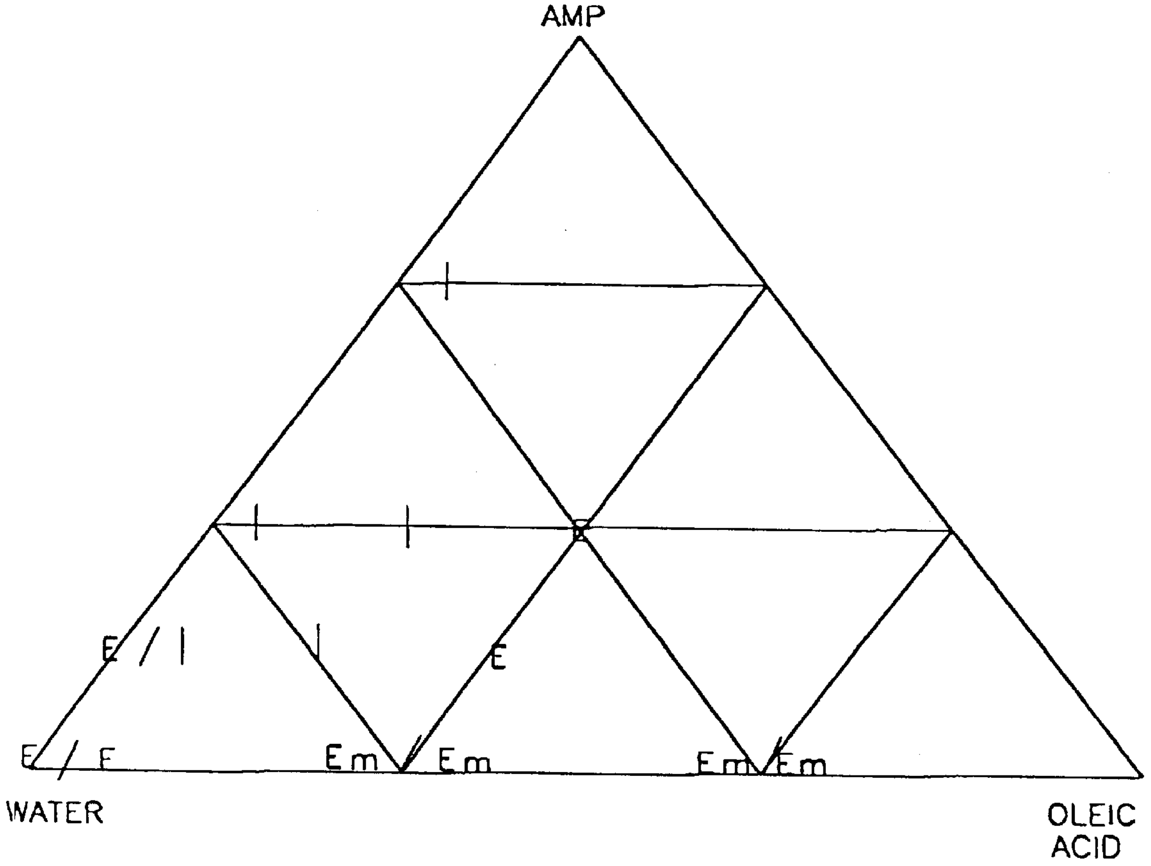
FIG. 8 is a phase diagram showing the liquid crystal characterization at 80° C. of the oleic acid soap compositions of the present invention having 5% by weight of $C_{12}$–$C_{14}$ linear alcohol ethoxylate having 4 moles EO.

As illustrated in FIGS. 4–10, the hexagonal region decreases as the temperature is increased. Accordingly, there appears to be a greater potential for transformation of the hexagonal liquid crystal into lamellar liquid crystals at higher temperatures. However, the soap compositions of the present invention maintains hexagonal phase over a broader temperature range than prior art compositions. For example, the prior art soap composition illustrated in FIG. 5 shows a large isotropic ("I") region in the 2–3% concentration range of oleic acid at 25° C. A soap composition of the present invention at the same concentration of oleic acid and temperature as shown in FIG. 6, is a mixture of isotropic ("I") and lamellar (D) phases but the D region extends across a larger area along the phase diagram. As illustrated in FIGS. 7 and 8, the temperature is increased to 60° C. and 80° C. respectively, in the compositions of the present invention, a large area of D and E phases remains.

Figure 9:
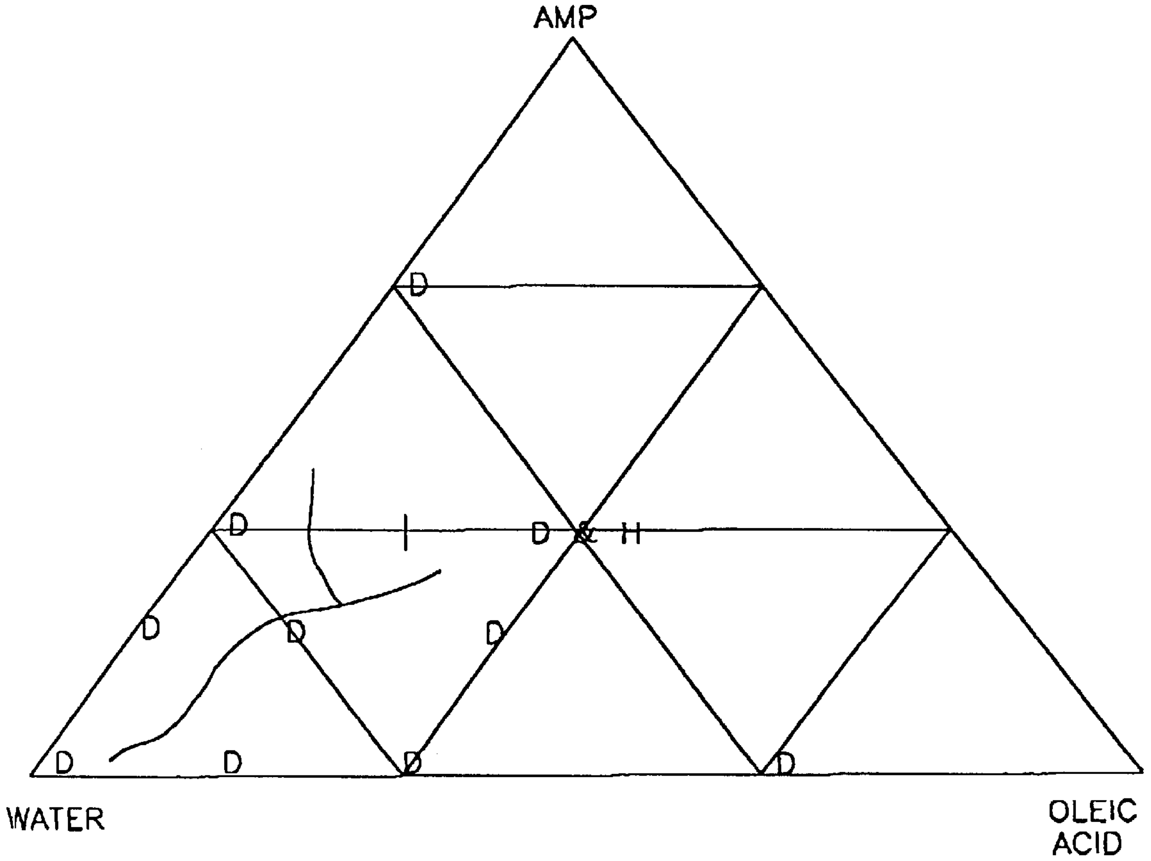
FIG. 9 is a phase diagram showing the liquid crystal characterization at 25° C. of oleic acid soap compositions of the present invention having 10% by weight of $C_{12}$–$C_{14}$ linear alcohol ethoxylate, 9 moles EO.
Figure 10:
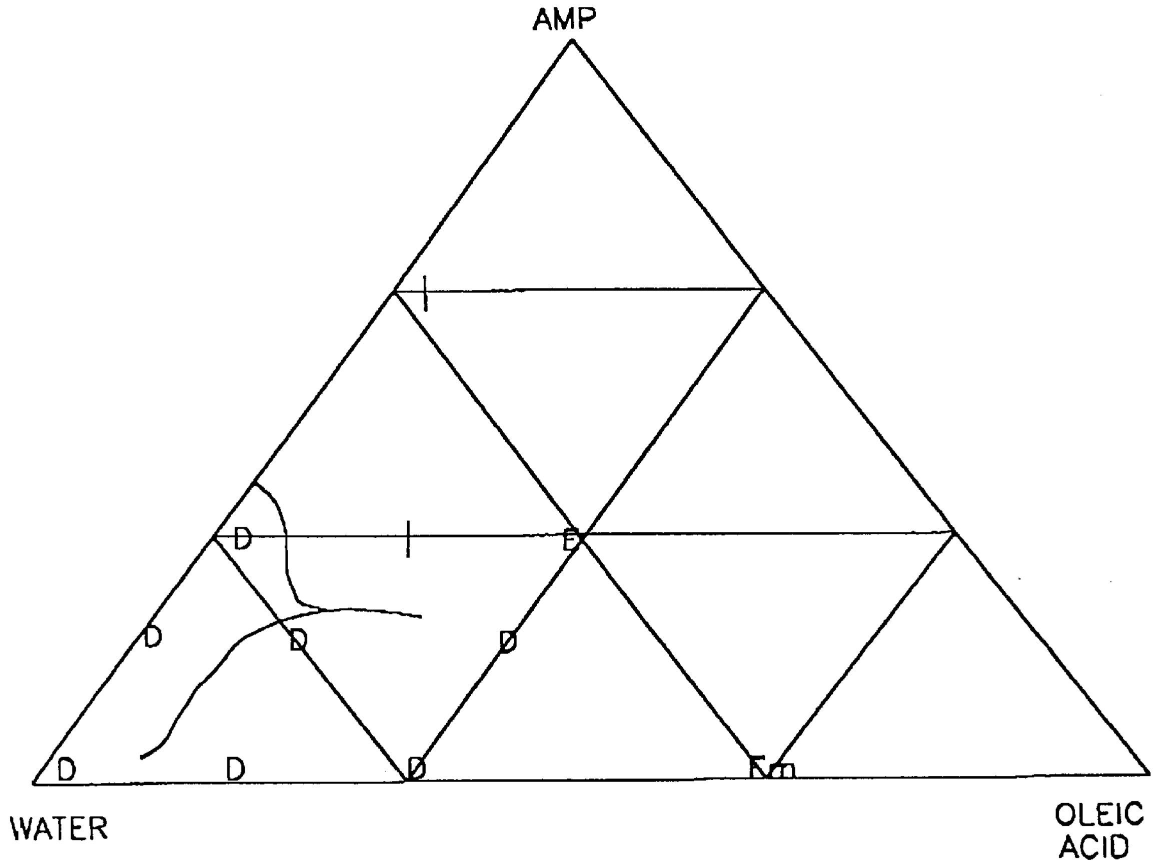
FIG. 10 is a phase diagram showing the liquid crystal characterization at 60° C. of oleic acid soap compositions of the present invention having 10% by weight of $C_{12}$–$C_{14}$ linear alcohol ethoxylate, 9 moles EQ.

In addition, in FIG. 9, a larger area of D and E regions are present in the 2–3% concentration range of oleic acid compositions of the present invention as compared to the prior art soap of FIG. 5. Again, when the temperature is increased to 60° C., as illustrated in FIG. 10, a majority of the D region remains in the compositions of the present invention.

This temperature stability property of the compositions of the present invention is highly desirable for storing and utilizing the compositions in a variety of temperature conditions.

Industrial Applicability

Therefore, the same soap composition may be used with a variety of additives to economically produce a number of different commercial cleaning and air fragrancing compositions which are robust, biodegradable and relatively insensitive to temperature changes.

Other modifications and variations of the present invention will become apparent to those skilled in the art from an examination of the above specification. Accordingly, other variations of the present invention may be made which fall within the scope of the appended Claims even though such variations were not specifically discussed above.

We claim:

1. An air fragrancing gel, consisting essentially of:

(a) an alkanolamine neutralized fatty acid;

(b) 1.0% to 35% by weight of at least one oil soluble fragrance composition; and (c) an effective amount of water to achieve a hydrophobic-hydrophilic balance necessary for liquid crystal formation;

wherein the oil soluble fragrance composition is essentially the sole solvent in the gel other than water and the air fragrancing gel has a temperature stability to at least about 80° C.

2. The air fragrancing gel as claimed in claim 1, wherein the fatty acid is present in an amount of from 0.1% to 90% by weight of the air fragrancing gel.

3.The air fragrancing gel as claimed in claim 1, wherein the fatty acid is present in an amount of about 5.0% by weight of the air fragrancing gel.

4. The air fragrancing gel in claim 1, wherein the fatty acid is saturated or unsaturated fatty acid having a carbon chain length of from $C_8$ to $C_{30}$.

5. The air fragrancing gel as claimed in claim 1, wherein the fatty acid is selected from the group consisting of stearic acid, oleic acid, palmitic acid, coconut oil, tall oil and mixtures thereof.

6. The air fragrancing gel as claimed in claim 1, where the fatty acid is oleic acid.

7. The air fragrancing gel as claimed in claim 1, wherein the alkanolamine is selected from the group consisting of 2-amino-2 methyl-1-propanol, 2-amino-1-butanol, tetrahydroxypropylethylenediamine, triisopropanolamine, triethanolamine, monoethanolamine, diisopropanolamine, diethanolamine and mixtures thereof.

8. The air fragrancing gel as claimed in claim 1, wherein the alkanolamine is selected from the group consisting of 2-amino-2-methyl-1-propanol, 2-amino-1-butanol, tetrahydroxypropylethylenediamine, triisopropanolamine and mixtures thereof.

9. The air fragrancing gel as claimed in claim 1, wherein the fragrance composition is present in an amount of from 5.0% to 25% by weight of the air fragrancing gel.

10. A method of fragrancing a locus, which comprises placing an effective amount of an air fragrancing composition into a location to be fragranced, the air fragrancing composition consisting essentially of:

(a) an alkanolamine neutralized fatty acid;

(b) from 1.0% to 35% by weight of at least one oil-soluble fragrance composition; and (c) an effective amount of water to achieve a hydrophobic-hydrophilic balance necessary for liquid crystal formation;

wherein the oil soluble fragrance composition is essentially the sole solvent in the air fragrancing composition other than water, and the air fragrancing composition has a temperature stability to at least about 80° C.

11. The method of fragrancing the air as claimed in claim 10, wherein the fatty acid is present in an amount of from 0.1% to 90% by weight of the air fragrancing composition.

12. The method of fragrancing the air as claimed in claim 10, wherein the fatty acid is present in an amount of about 5.0% by weight of the air fragrancing composition.

13. The method of fragrancing the air as claimed in claim 10, wherein the fatty acid is saturated or unsaturated fatty acid having a carbon chain length of from about $C_8$ to about $C_{30}$.

14. The method of fragrancing the air as claimed in claim 10, wherein the fatty acid is selected from the group consisting of stearic acid, oleic acid, palmitic acid, coconut oil, tall oil and mixtures thereof.

15. The method of fragrancing the air as claimed in claim 10, wherein the alkanolamine is selected from the group consisting of 2-amino-2 methyl-1-propanol, 2-amino-1-butanol, tetrahydroxypropylethylenedimine, triisopropanolamine, monoethanolamine, diisopropanolamine, diethanolamine and mixtures thereof.

16. The method of fragrancing the air as claimed in claim 10, wherein the alkanolamine is selected from the group consisting of 2-amino-2-methyl-1-propanol, 2-amino-1-butanol, tetrahydroxypropylethylenediamine, triisopropanolamine and mixtures thereof.

17. The method of fragrancing a locus as claimed in claim 10, wherein the fragrance composition is present in an amount of from 5.0% to 25% by weight of the air fragrancing composition.

* * * * *